(12) United States Patent
O'Dea et al.

(10) Patent No.: US 8,771,207 B2
(45) Date of Patent: Jul. 8, 2014

(54) DEVICE AND A SYSTEM FOR USE IN A PROCEDURE FOR IMPROVING A SEALING FUNCTION OF A SPHINCTER AND A METHOD FOR IMPROVING THE SEALING FUNCTION OF A SPHINCTER

(75) Inventors: John O'Dea, Bearna (IE); Adrian McHugh, Kilcolgen (IE); Patrick Griffin, Castlegar (IE)

(73) Assignee: Flip Technologies Limited, Galway (IE)

( * ) Notice: Subject to any disclaimer, the term of this patent is extended or adjusted under 35 U.S.C. 154(b) by 1057 days.

(21) Appl. No.: 12/665,448

(22) PCT Filed: Jun. 27, 2008

(86) PCT No.: PCT/IE2008/000067
§ 371 (c)(1),
(2), (4) Date: Mar. 17, 2010

(87) PCT Pub. No.: WO2009/001325
PCT Pub. Date: Dec. 31, 2008

(65) Prior Publication Data
US 2010/0228192 A1    Sep. 9, 2010

(30) Foreign Application Priority Data

Jun. 27, 2007 (IE) .................................. S2007/0461
Jun. 27, 2007 (IE) .................................. S2007/0463
Nov. 19, 2007 (IE) .................................. S2007/0842

(51) Int. Cl.
*A61B 5/103* (2006.01)
*A61M 29/00* (2006.01)

(52) U.S. Cl.
USPC .......................... 600/593; 604/104; 606/192

(58) Field of Classification Search
USPC .................. 606/192; 604/100.3, 104, 100.03; 600/593
See application file for complete search history.

(56) References Cited

U.S. PATENT DOCUMENTS 4,587,975 A    5/1986    Salo
6,773,452 B2*  8/2004    Shaker .......................... 600/587

FOREIGN PATENT DOCUMENTS

| WO | 2004075928 A2 | 9/2004 |
|----|---------------|--------|
| WO | 2006002635 A1 | 1/2006 |
| WO | 2006090351 A1 | 8/2006 |

OTHER PUBLICATIONS

International Search Report for PCT/IE2008/000067 Nov. 6, 2008.

*Primary Examiner* — Katherine Dowe
(74) *Attorney, Agent, or Firm* — Sughrue Mion, PLLC

(57) ABSTRACT

A system (1) and a device (3) is used in a fundoplication procedure in order to avoid over-tightening of the fundus of the stomach when the fundus is being wrapped around the esophagus (7) adjacent the lower oesophageal sphincter (5). The device (3) comprises a catheter (8) having a primary balloon (12) located at a distal end (9) thereof which is inflatable with a saline solution by a primary pump (26). A pair of spaced apart primary stimulating electrodes (32) on the catheter (8) within the primary balloon (12) receive a stimulating current signal from a constant current signal generator (40) under the control of a microprocessor (43), which reads voltage signals from spaced apart primary receiving electrodes (35) on the catheter (8) in the balloon (12). The microprocessor (43) determines the diameter of the primary balloon (12) at locations adjacent the primary receiving electrodes (35), and an image (47) of the inflated primary balloon (12) is displayed on a visual display screen (48) along with corresponding diameter values of the primary balloon (12). The primary balloon (12) is located in the sphincter (5) and inflated with the saline solution until the sphincter (5) has been dilated to a desired diameter, which is observed on the visual display screen (45). As the fundus of the stomach is being wrapped around the esophagus (7) adjacent the sphincter (5) the diameter of the primary balloon (12) is observed so that the fundus is not over-tightened. A secondary balloon (50) on the catheter (8) is independently inflatable for simulating a bolus of food in the esophagus (7) so that the dilating response of the sphincter (5) can be determined by observing the image (47) of the primary balloon (12) and the diameter values thereof on the visual display screen (45).

3 Claims, 5 Drawing Sheets

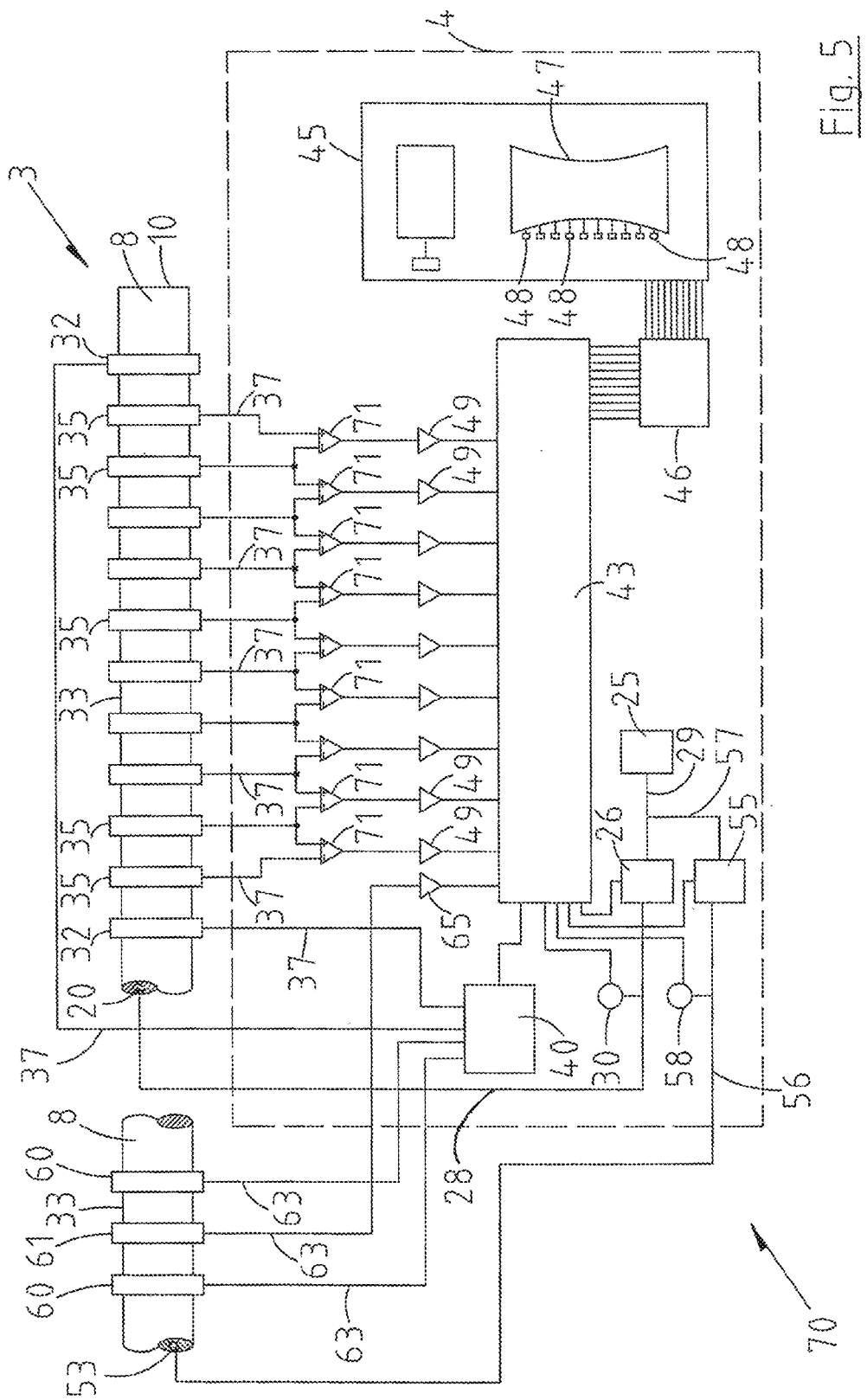

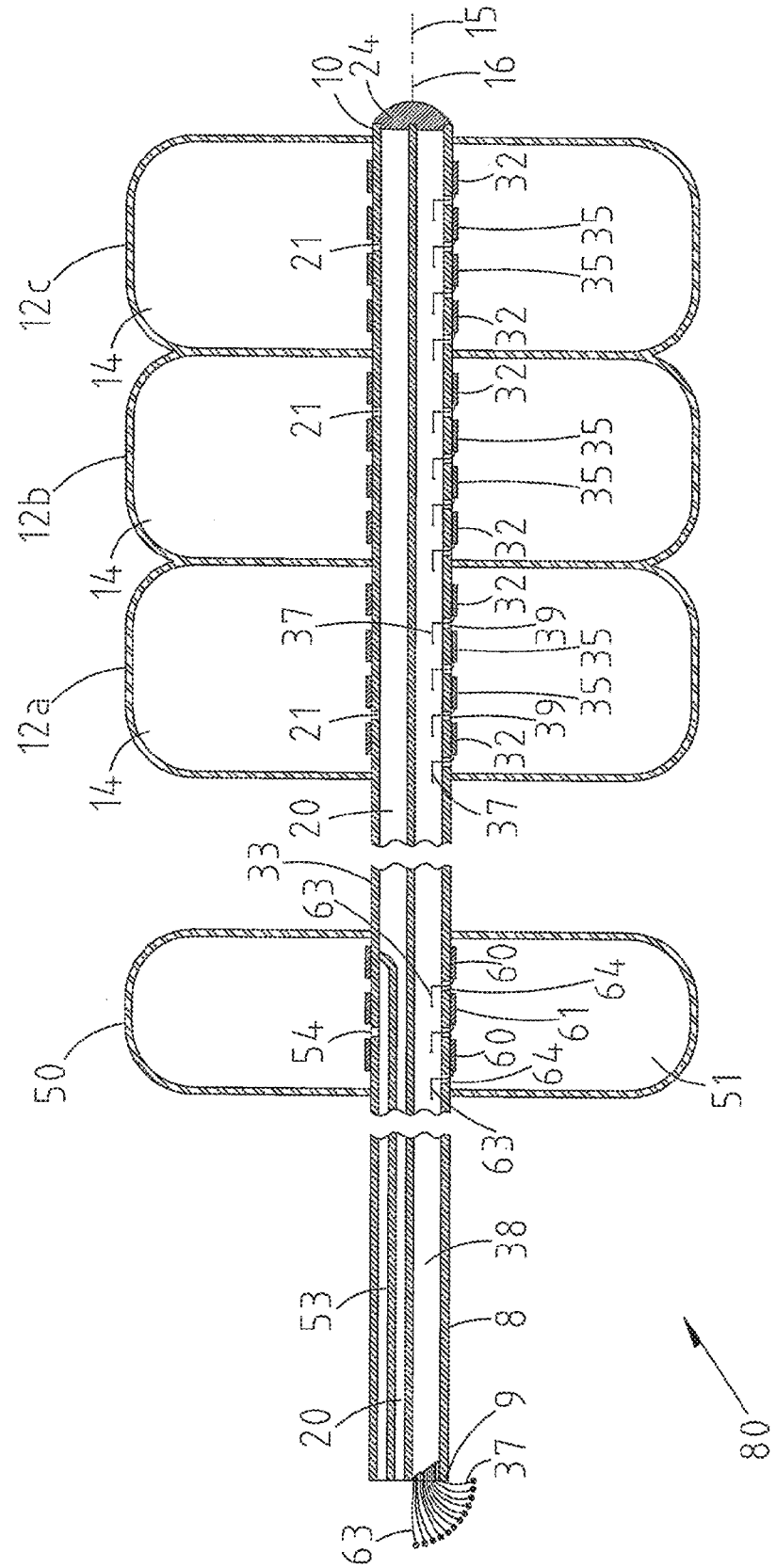

Figure 1:
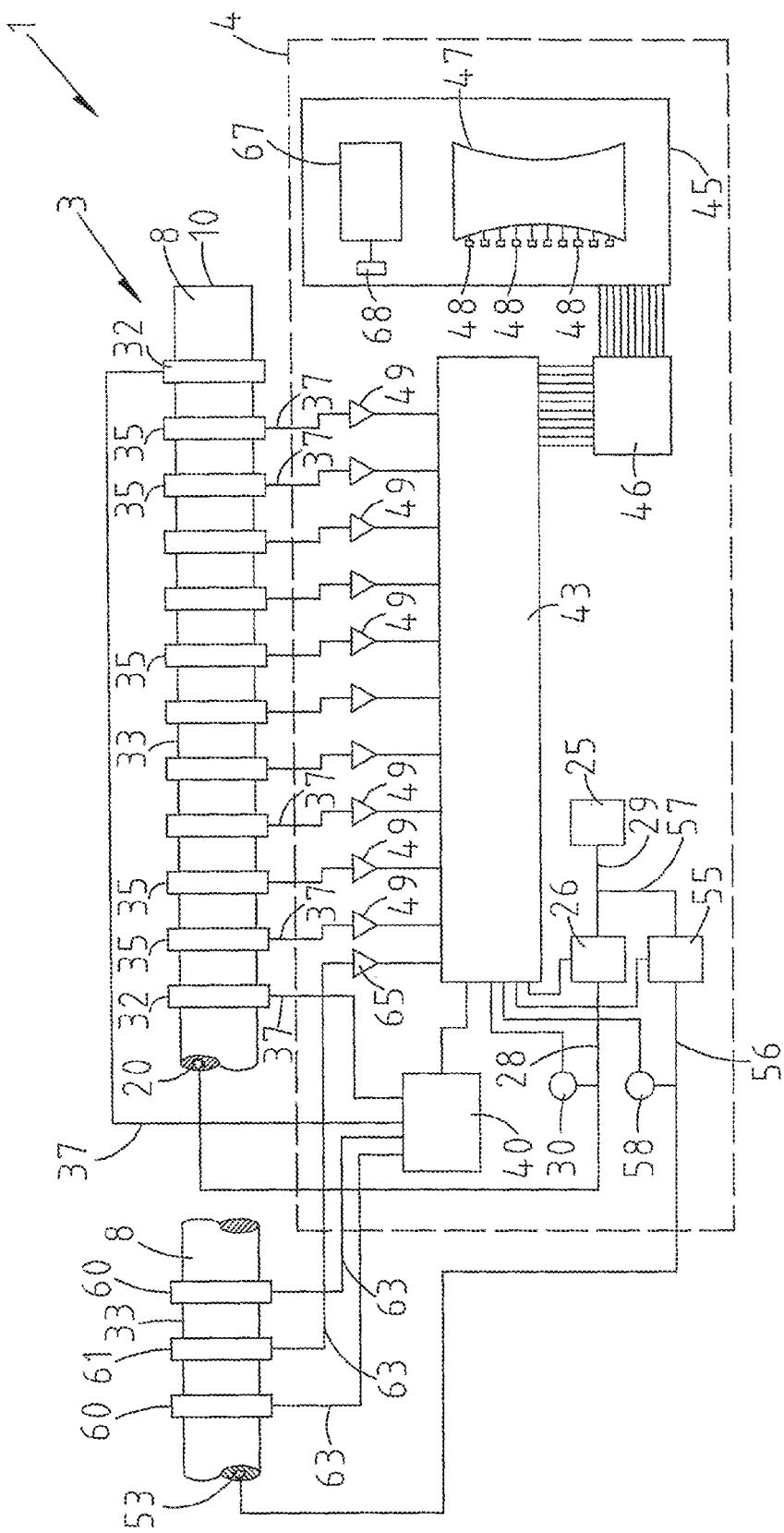

DEVICE AND A SYSTEM FOR USE IN A PROCEDURE FOR IMPROVING A SEALING FUNCTION OF A SPHINCTER AND A METHOD FOR IMPROVING THE SEALING FUNCTION OF A SPHINCTER

The present invention relates to a device and a system for use in a procedure for improving the sealing function of a sphincter, and in particular, though not limited to a device and a system for use in a procedure for improving the sealing function of the lower oesophageal sphincter. The present invention also relates to a method for improving the sealing function of a sphincter, and in particular, though not limited to a method for improving the sealing function of the lower oesophageal sphincter. The invention also relates to a device and a system for testing the dilating response of a sphincter, and in particular, though not limited to a device and a system for testing the dilating response of a lower oesophageal sphincter in response to a simulated bolus of food, and the invention further relates to a method for testing the dilating response of a sphincter.

Gastroesophageal reflux disease (GERD), sometimes commonly referred to as heartburn is due to a failure of the lower oesophageal sphincter to function as intended. This sphincter is located at the lower end of the oesophagus between the oesophagus and the stomach, and along with diaphragm muscles, and indeed the sling fibres at the top of the stomach, serves the critical function of preventing the contents of the stomach being aspirated into the oesophagus. In many cases the only means of treating GERD is to perform a surgical procedure known as fundoplication. During fundoplication surgery, the fundus or upper part of the stomach (the fundus) is wrapped around the lower portion of the oesophagus adjacent the sphincter and sutured into place so that the lower portion of the oesophagus passes through a small tunnel of stomach muscle. This surgery strengthens the sphincter and augments the biomechanical sealing function of the sphincter, thereby minimising and in general preventing the aspiration of acid from the stomach into the oesophagus.

By its nature fundoplication procedures tend to be operator dependent, with success rates varying somewhere between 50% and 80%. Success is defined as the absence of a requirement for drugs for symptomatic relief. Such a low success rate is undesirable. In order to maximise the success rate there is a tendency to over-tighten the fundus around the oesophagus. A common side effect of over-tightening the fundus around the oesophagus in a fundoplication procedure is that a subject may subsequently experience difficulty in swallowing food. Food is passed through the oesophagus of a normal subject as a food bolus by a peristaltic pumping action. The peristaltic pumping action of the oesophagus causes the lower oesophageal sphincter to dilate in preparation of the food being delivered to the stomach. Thus, if the fundus is wrapped and sutured too tightly around the oesophagus adjacent the sphincter, the amount to which the sphincter can dilate is reduced, thereby presenting a restriction to the food bolus, which in turn leads to difficulty in swallowing.

There is therefore a need for a device and a system which reduces the probability of over-tightening of the fundus around the oesophagus adjacent the sphincter during a fundoplication procedure, or any other procedure for enhancing the biomechanical function of the lower oesophageal sphincter or any other sphincter.

The present invention is directed towards providing a device and a system for use in a procedure for improving the sealing function or enhancing the biomechanical function of a sphincter which addresses the problems discussed above with reference to the lower oesophageal sphincter, and similar problems which may arise in procedures for improving the sealing function of other sphincters. The invention is also directed towards a method for improving the sealing function or enhancing the biomechanical function of a sphincter, and to a method for improving the sealing function or enhancing the biomechanical function of the lower oesophageal sphincter.

The invention is also directed towards providing a device and a system for testing the dilating response of a sphincter, and also for testing the dilating response of a lower oesophageal sphincter in response to a simulated bolus of food, and the invention is also directed towards providing a method for testing the dilating response of a sphincter.

According to the invention there is provided a device for use in a procedure for improving a sealing function of a sphincter, the device comprising a catheter extending between a proximal end and a distal end, a primary expandable element located on the catheter towards the distal end thereof for inserting in the sphincter, and a primary measuring means associated with the primary expandable element for facilitating determining the transverse cross-sectional area of the primary expandable element, the primary expandable element being selectively operable in one of a first mode for dilating the sphincter to a desired transverse cross-sectional area, and the primary measuring means being operable for providing an indication of the transverse cross-sectional area of the sphincter while the procedure for improving the sealing function thereof is being carried out, and a second mode for progressively expanding with the sphincter as the sphincter is dilating for determining the dilated transverse cross-sectional area of the sphincter in response to stimulation thereof.

In one embodiment of the invention the primary expandable element defines a hollow interior region, and the primary measuring means is located in the hollow interior region thereof.

Preferably, the primary measuring means is adapted for determining the transverse cross-sectional area of the primary expandable element.

In one embodiment of the invention the primary expandable element comprises a primary inflatable balloon, defining the hollow interior region, and the catheter extends through the hollow interior region of the primary balloon.

In another embodiment of the invention the primary balloon when inflated is of cylindrical configuration defining a central longitudinal axis coinciding with a central longitudinal axis of the catheter.

Preferably, a primary inflating medium accommodating means is provided for accommodating an inflating medium to the primary balloon for inflating thereof.

Advantageously, the primary inflating medium accommodating means comprises a primary axial communicating bore extending axially through the catheter from the proximal end thereof for accommodating the inflating medium to the primary balloon.

Preferably, at least one primary radial communicating bore extends through the catheter from the primary axial communicating bore communicating the primary axial communicating bore with the hollow interior region of the primary balloon for accommodating the inflating medium into the primary balloon.

In one embodiment of the invention the primary measuring means comprises at least one primary stimulating electrode located on one of the catheter and an inner surface of the primary balloon and at least one primary receiving electrode located on one of the catheter and the inner surface of the primary balloon and axially spaced apart and insulated from the primary stimulating electrode, the at least one primary receiving electrode being responsive to a stimulating signal applied to the at least one primary stimulating electrode for producing a resulting signal indicative of the transverse cross-sectional area of the primary balloon when the primary balloon is inflated with an electrically conductive inflating medium. Advantageously, a pair of axially spaced apart mutually insulated primary stimulating electrodes are provided, and a plurality of axially spaced apart mutually insulated primary receiving electrodes are provided between the primary stimulating electrodes and axially spaced apart therefrom for producing respective resulting signals indicative of the transverse cross-sectional area of the primary balloon adjacent the corresponding primary receiving electrodes in response to a stimulating signal applied across the primary stimulating electrodes when the primary balloon is inflated with an electrically conductive inflating medium.

Ideally, each primary stimulating electrode and each primary receiving electrode is provided on the catheter.

In one embodiment of the invention each primary stimulating electrode comprises an electrically conductive band extending around the catheter. Preferably, each primary stimulating electrode comprises an electrically conductive band extending completely around the catheter. Advantageously, each primary receiving electrode comprises an electrically conductive band extending around the catheter.

Ideally, each primary receiving electrode comprises an electrically conductive band extending completely around the catheter.

In one embodiment of the invention a primary electrically conductive means is electrically coupled to the at least one primary stimulating electrode and to the at least one primary receiving electrode, the primary electrically conductive means being adapted for communicating a stimulating signal to the at least one primary stimulating electrode, and for receiving a resulting signal from the at least one primary receiving electrode in response to the stimulating signal. Preferably, the primary electrically conductive means extends to the proximal end of the catheter. Advantageously, a primary axial wire accommodating bore extends through the catheter from the proximal end thereof for accommodating the primary electrically conductive means from the proximal end of the catheter to the primary stimulating and receiving electrodes. Ideally, the primary electrically conductive means comprises a plurality of mutually insulated primary electrically conductive wires, each coupled to a corresponding one of the primary stimulating and receiving electrodes.

In another embodiment of the invention the primary expandable element comprises at least two primary balloons located adjacent each other on the catheter, each primary balloon defining a hollow interior region through which the catheter extends, and a primary measuring means being located in each primary balloon for determining the transverse cross-sectional area of the corresponding primary balloon.

Preferably, the respective primary balloons are inflatable independently of each other, and respective primary inflating medium accommodating means are provided for the respective primary balloons for independent inflating thereof.

Advantageously, the primary expandable element is adapted for locating in a lower oesophageal sphincter for use in a procedure for enhancing the biomechanical function of the lower oesophageal sphincter.

In one embodiment of the invention the primary expandable element is adapted for locating in a lower oesophageal sphincter for use in a fundoplication procedure.

In another embodiment of the invention a stimulating means is provided for stimulating the sphincter to dilate when the primary expandable element is operated in the second mode. Preferably, the stimulating means comprises a secondary expandable element located on the catheter. Advantageously, the secondary expandable element is located on the catheter intermediate the primary expandable element and the proximal end of the catheter. Ideally, the secondary expandable element is axially spaced apart from the primary expandable element.

In one embodiment of the invention the secondary expandable element comprises a secondary inflatable balloon defining a hollow interior region, with the catheter extending through the hollow interior region thereof, the secondary balloon being inflatable independently of the primary balloon. Preferably, the secondary balloon is located coaxially with the catheter.

In another embodiment of the invention a secondary inflating medium accommodating means is provided for accommodating an inflating medium to the secondary balloon for inflating thereof. Preferably, the secondary inflating medium accommodating means comprises a secondary axial communicating bore extending through the catheter from the proximal end thereof and communicating with the hollow interior region of the secondary balloon for accommodating the inflating medium to the secondary balloon for inflating thereof. Advantageously, at least one secondary radial communicating bore extending through the catheter communicates the secondary axial communicating bore with the hollow interior region of the secondary balloon.

In another embodiment of the invention a secondary measuring means is provided for measuring the transverse cross-sectional area of the secondary balloon. Preferably, the secondary measuring means is located in the hollow interior region of the secondary balloon. Advantageously, the secondary measuring means comprises at least one secondary stimulating electrode located on one of the catheter and the inner surface of the secondary balloon and at least one secondary receiving electrode located on one of the catheter and the inner surface of the secondary balloon and axially spaced apart and insulated from the secondary stimulating electrode, the at least one secondary receiving electrode being responsive to a stimulating signal applied to the at least one secondary stimulating electrode for producing a resulting signal indicative of the transverse cross-sectional area of the secondary balloon when the secondary balloon is inflated with an electrically conductive inflating medium. Ideally, a pair of axially spaced apart mutually insulated secondary stimulating electrodes are provided, and a plurality of axially spaced apart mutually insulated secondary receiving electrodes are provided between the secondary stimulating electrodes and axially spaced apart therefrom for producing respective resulting electrical signals indicative of the transverse cross-sectional area of the secondary balloon adjacent the corresponding secondary receiving electrodes in response to a stimulating signal applied across the secondary stimulating electrodes when the secondary balloon is inflated with an electrically conductive inflating medium.

In one embodiment of the invention each secondary stimulating electrode and each secondary receiving electrode is located on the catheter. Preferably, each secondary stimulating electrode comprises an electrically conductive band extending around the catheter. Advantageously, each secondary stimulating electrode comprises an electrically conductive band extending completely around the catheter. Preferably, each secondary receiving electrode comprises an electrically conductive band extending around the catheter.

Ideally, each secondary receiving electrode comprises an electrically conductive band extending completely around the catheter.

In one embodiment of the invention a secondary electrically conductive means is electrically coupled to the at least one secondary stimulating electrode and to the at least one secondary receiving electrode, the secondary electrically conductive means being adapted for communicating a stimulating signal to the at least one secondary stimulating electrode, and for receiving a resulting signal from the at least one secondary receiving electrode in response to the stimulating signal. Preferably, the secondary electrically conductive means comprises a plurality of mutually insulated electrically conductive wires coupled to the respective secondary stimulating and receiving electrodes. Advantageously, the secondary electrically conductive wires are accommodated from the proximal end of the catheter to the corresponding respective secondary stimulating and receiving electrodes through the primary axial wire accommodating bore.

In one embodiment of the invention at least one secondary radial wire accommodating bore extends radially through the catheter from the primary axial wire accommodating bore for accommodating the secondary electrically conductive wires from the primary axial wire accommodating bore to the secondary stimulating and receiving electrodes.

In one embodiment of the invention the secondary expandable element is adapted for simulating a bolus of food in the oesophagus for stimulating the lower oesophageal sphincter for dilating thereof.

The invention also provides a system for use in a procedure for improving a sealing function of a sphincter, the system comprising a catheter extending between a proximal end and a distal end, a primary expandable element located on the catheter adjacent the distal end thereof for inserting in the sphincter, a primary measuring means associated with the primary expandable element for producing a signal indicative of the transverse cross-section of the primary expandable element, and a control means responsive to signals from the primary measuring means for determining the transverse cross-sectional area of the primary expandable element, the primary expandable element being selectively operable in one of a first mode for dilating the sphincter to a desired transverse cross-sectional area, and the primary measuring means being operable for providing an indication of the transverse cross-sectional area of the sphincter while the procedure for improving the sealing function thereof is being carried out, and a second mode for progressively expanding with the sphincter as the sphincter is dilating for determining the dilated transverse cross-sectional area of the sphincter in response to stimulation thereof.

In one embodiment of the invention a display means operating under the control of the control means is provided for displaying an image representative of the primary expandable element for providing the indication of the transverse cross-sectional area of the sphincter while the procedure is being carried out. Preferably, the display means is operated under the control of the control means for displaying the image representative of the primary expandable element as a three-dimensional representation. Advantageously, the display means is operated under the control of the control means for displaying the diameter of the primary expandable element at at least one transverse cross-section thereof.

In one embodiment of the invention the display means is operated under the control of the control means for displaying the diameter of the primary expandable element at a plurality of axially spaced apart transverse cross-sections thereof.

In one embodiment of the invention a primary inflating means is provided for inflating the primary balloon with an inflating medium. Preferably, the primary inflating means is operable for maintaining the primary balloon at one of substantially constant volume and substantially constant pressure when the primary expandable element is being operated in the first mode.

Advantageously, the primary inflating means is operable for maintaining the primary balloon at one of substantially constant volume and substantially constant pressure when the primary expandable element is operating in the second mode.

In one embodiment of the invention a primary inflating medium accommodating means is provided for accommodating the inflating medium from the primary inflating means to the primary balloon for inflating thereof.

In one embodiment of the invention the primary measuring means comprises at least one primary stimulating electrode located on one of the catheter and an inner surface of the primary balloon and at least one primary receiving electrode located on one of the catheter and the inner surface of the primary balloon and axially spaced apart and insulated from the primary stimulating electrode, the at least one primary receiving electrode being responsive to a stimulating signal applied by the control means to the at least one primary stimulating electrode for producing a resulting signal indicative of the transverse cross-sectional area of the primary balloon when the primary balloon is inflated with an electrically conductive inflating medium.

Preferably, a pair of axially spaced apart mutually insulated primary stimulating electrodes are provided, and a plurality of axially spaced apart mutually insulated primary receiving electrodes are provided between the primary stimulating electrodes and axially spaced apart therefrom for producing respective resulting signals indicative of the transverse cross-sectional area of the primary balloon adjacent the corresponding primary receiving electrodes in response to a stimulating signal applied by the control means across the primary stimulating electrodes when the primary balloon is inflated with an electrically conductive inflating medium.

Advantageously, the control means is responsive to the resulting signals on the at least one primary receiving electrodes for determining the transverse cross-sectional area of the primary balloon.

In another embodiment of the invention a primary electrically conductive means electrically couples the at least one primary stimulating electrode and the at least one primary receiving electrode to the control means for communicating one of a stimulating voltage signal and a stimulating current signal to the at least one primary stimulating electrode, and for receiving a resulting signal from the at least one primary receiving electrode in response to the stimulating signal.

Advantageously, the primary electrically conductive means extends from the primary stimulating and receiving electrodes to the proximal end of the catheter for coupling to the control means.

In a further embodiment of the invention the primary expandable element comprises at least two primary balloons located adjacent each other on the catheter, each primary balloon defining a hollow interior region through which the catheter extends, and a primary measuring means being located in each primary balloon for determining the transverse cross-sectional area of the corresponding primary balloon. Preferably, the respective primary balloons are inflatable independently of each other. Advantageously, respective primary inflating medium accommodating means are provided for the respective primary balloons for independent inflating thereof. Ideally, the display means is adapted for displaying an image representative of the respective balloons.

In one embodiment of the invention the primary expandable element is adapted for locating in a lower oesophageal sphincter.

In one embodiment of the invention a stimulating means is provided for stimulating the sphincter to dilate when the primary expandable element is operating in the second mode, and preferably, the stimulating means comprises a secondary expandable element located on the catheter.

In one embodiment of the invention the secondary expandable element comprises a secondary inflatable balloon defining a hollow interior region with the catheter extending through the hollow interior region thereof, the secondary balloon being inflatable independently of the primary balloon.

In one embodiment of the invention a secondary inflating means is provided for inflating the secondary balloon with an inflating medium when the primary expandable element is being operated in the second mode. Preferably, a secondary inflating medium accommodating means is provided for accommodating an inflating medium from the secondary inflating means to the secondary balloon for inflating thereof.

In one embodiment of the invention the secondary inflating medium accommodating means comprises a secondary axial communicating bore extending through the catheter from the proximal end thereof and communicating with the hollow interior region of the secondary balloon for accommodating the inflating medium to the secondary balloon for inflating thereof.

In another embodiment of the invention a secondary measuring means is provided for measuring the transverse cross-sectional area of the secondary balloon and for producing a signal indicative of the transverse cross-sectional area of the secondary expandable element, the control means being responsive to the signal from the secondary measuring means for determining the transverse cross-sectional area of the secondary balloon.

Preferably, the display means is operated under the control of the control means for displaying an image representative of the secondary balloon. Advantageously, the display means is operated under the control of the control means for displaying the image representative of the secondary balloon as a three-dimensional representation.

In one embodiment of the invention the display means is operated under the control of the control means for displaying the diameter of the secondary balloon at least one transverse cross-section thereof.

Preferably, the display means is operated under the control of the control means for displaying the diameter of the secondary balloon at a plurality of axially spaced apart transverse cross-sections thereof.

In one embodiment of the invention the secondary measuring means is located in the hollow interior region of the secondary balloon.

In another embodiment of the invention the secondary measuring means comprises at least one secondary stimulating electrode located on one of the catheter and the inner surface of the secondary balloon and at least one secondary receiving electrode located on one of the catheter and the inner surface of the secondary balloon and axially spaced apart and insulated from the secondary stimulating electrode, the at least one secondary receiving electrode being responsive to a stimulating signal applied by the control means to the at least one secondary stimulating electrode for producing the resulting signal indicative of the transverse cross-sectional area of the secondary balloon when the secondary balloon is inflated with an electrically conductive inflating medium. Preferably, a pair of axially spaced apart mutually insulated secondary stimulating electrodes are provided, and a plurality of axially spaced apart mutually insulated secondary receiving electrodes are provided between the secondary stimulating electrodes and axially spaced apart therefrom for producing respective resulting signals indicative of the transverse cross-sectional area of the secondary balloon adjacent the corresponding secondary receiving electrodes in response to a stimulating signal applied by the control means across the secondary stimulating electrodes when the secondary balloon is inflated with an electrically conductive inflating medium.

In another embodiment of the invention a secondary electrically conductive means electrically couples the at least one secondary stimulating electrode and the at least one secondary receiving electrode to the control means for communicating one of a stimulating voltage signal and a stimulating current signal to the at least one secondary stimulating electrode, and for receiving a resulting signal from the at least one secondary receiving electrode in response to the stimulating signal.

Preferably, the secondary electrically conductive means comprises a plurality of mutually insulated electrically conductive wires coupled to the respective secondary stimulating and receiving electrodes and to the control means.

In another embodiment of the invention a secondary pressure monitoring means is provided for monitoring the pressure of the inflating medium in the secondary balloon.

In a further embodiment of the invention the secondary expandable element is adapted for simulating a bolus of food in the oesophagus for stimulating the lower oesophageal sphincter for dilating thereof when the primary expandable element is being operated in the second mode.

In another embodiment of the invention a primary pressure monitoring means is provided for monitoring the pressure of the inflating means in the primary balloon.

In one embodiment of the invention the system is adapted for use in carrying out a procedure for enhancing the biomechanical function of the lower oesophageal sphincter.

In another embodiment of the invention the system is adapted for use in a fundoplication procedure.

In a further embodiment of the invention the system is adapted for use in determining the dilated transverse cross-sectional area of a lower oesophageal sphincter in response to stimulation thereof.

Further the invention provides use of the device according to the invention in a procedure for enhancing the biomechanical function of the lower oesophageal sphincter.

The invention further provides use of the device according to the invention in a fundoplication procedure.

The invention also provides use of the device according to the invention in determining the dilated transverse cross-sectional area of a lower oesophageal sphincter in response to stimulation thereof.

The invention also provides use of the system according to the invention in a procedure for enhancing the biomechanical function of the lower oesophageal sphincter.

Further the invention provides use of the system according to the invention in a fundoplication procedure.

The invention also provides use of the system according to the invention in determining the dilated transverse cross-sectional area of a lower oesophageal sphincter in response to stimulation thereof.

The invention also provides a method for improving a sealing function of a sphincter, the method comprising dilating the sphincter to a desired transverse cross-sectional area, and carrying out a procedure to enhance the biomechanical function of the sphincter while the sphincter is dilated to the desired transverse cross-sectional area.

Preferably, a dilating means is located in the sphincter for dilating the sphincter to the desired transverse cross-sectional area. Advantageously, the dilating means is operated at one of substantially constant volume and substantially constant pressure during the carrying out of the procedure.

Advantageously, the dilating means is located towards a distal end of an elongated catheter extending between a proximal end and the distal end.

In one embodiment of the invention the dilating means comprises a primary expandable element.

In another embodiment of the invention a means is provided for expanding the primary expandable element.

Preferably, the primary expandable element comprises a primary inflatable balloon defining a hollow interior region with the catheter extending therethrough.

Advantageously, the primary balloon is inflated with an inflating medium until the sphincter has been dilated to the desired transverse cross-sectional area.

In one embodiment of the invention a primary measuring means associated with the primary balloon is provided for determining the transverse cross-sectional area of the primary balloon, and the primary measuring means produces a signal indicative of the transverse cross-sectional area of the primary balloon.

In another embodiment of the invention the primary measuring means is located in the primary balloon.

Preferably, the primary measuring means in the primary balloon comprises at least one primary stimulating electrode on one of the catheter and an inner surface of the primary balloon and at least one primary receiving electrode on the one of the catheter and the inner surface of the primary balloon axially spaced apart from the primary stimulating electrode, so that when the primary balloon is inflated with an electrically conductive medium and one of a stimulating voltage signal and a stimulating current signal is applied to the at least one primary stimulating electrode, a resulting signal on the at least one primary receiving electrode is indicative of the transverse cross-sectional area of the primary balloon.

Advantageously, the primary measuring means in the primary balloon comprises a pair of primary stimulating electrodes axially spaced apart from each other, and a plurality of axially spaced apart primary receiving electrodes located between the primary stimulating electrodes and spaced apart therefrom, so that when one of a stimulating voltage signal and a stimulating current signal is applied across the primary stimulating electrodes when the primary balloon is inflated with the electrically conductive medium, the resulting signals on the primary receiving electrodes are indicative of the transverse cross-sectional area of the primary balloon adjacent the corresponding primary receiving electrodes.

Ideally, one of a stimulating voltage signal and a stimulating current signal is applied to the at least one primary stimulating electrode and the resulting signal is read from the at least one primary receiving electrode, and the transverse cross-sectional area of the primary balloon adjacent the corresponding at least one primary receiving electrode is determined from the signal read from the at least one primary receiving electrode.

In another embodiment of the invention a display means is provided for displaying an image representative of the primary balloon, the image being prepared from the signals read from the primary measuring means, and the image is observed during the carrying out of the procedure to enhance the biomechanical function of the sphincter so that the sphincter is at the desired transverse cross-sectional area when the procedure is being carried out.

Preferably, the diameter of the primary balloon at least one transverse cross-section is displayed on the display means.

Advantageously, the sphincter is a lower oesophageal sphincter, and the procedure to enhance the biomechanical function of the sphincter is a procedure for tightening the sphincter.

In another embodiment of the invention the sphincter is a lower oesophageal sphincter, and the procedure to enhance the biomechanical function of the sphincter is a fundoplication procedure.

The invention also provides a method for determining the dilating function of a sphincter, the method comprising locating a primary expandable element in the sphincter, stimulating the sphincter to dilate, permitting the primary expandable element to progressively expand with the dilating sphincter, and monitoring the transverse cross-sectional area of the expanding primary expandable element for determining the transverse cross-sectional area of the sphincter when dilated.

Preferably, the primary expandable element comprises a primary inflatable balloon located towards a distal end of an elongated catheter extending between a proximal end and the distal end.

Advantageously, the primary balloon defines a hollow interior region with the catheter extending through the hollow interior region of the balloon.

Advantageously, a primary measuring means is provided for determining the transverse cross-sectional area of the primary balloon, and for producing a signal indicative of the transverse cross-sectional area of the balloon.

In one embodiment of the invention the primary measuring means is located in the primary balloon.

In another embodiment of the invention the primary measuring means comprises at least one primary stimulating electrode on one of the catheter and an inner surface of the primary balloon and at least one primary receiving electrode on the one of the catheter and the inner surface of the primary balloon so that when the primary balloon is inflated with an electrically conductive medium and one of a stimulating voltage signal and a stimulating current signal is applied to the at least one primary stimulating electrode, a resulting signal on the at least one primary receiving electrode is indicative of the transverse cross-sectional area of the primary balloon adjacent the location of the at least one primary receiving electrode.

Preferably, the primary measuring means in the primary balloon comprises a pair of primary stimulating electrodes axially spaced apart from each other, and a plurality of axially spaced apart primary receiving electrodes located between the primary stimulating electrodes and spaced apart therefrom so that when one of a stimulating voltage signal and a stimulating current signal is applied across the primary stimulating electrodes when the primary balloon is inflated with the electrically conductive medium, the resulting voltage on the primary receiving electrodes is indicative of the transverse cross-sectional area of the primary balloon adjacent the respective corresponding primary receiving electrodes.

Ideally, a stimulating current signal is applied to the at least one primary stimulating electrode and a resulting signal is read from the at least one primary receiving electrode to determine the transverse cross-sectional area of the primary balloon adjacent the at least one primary receiving electrode.

In another embodiment of the invention a display means is provided for displaying an image representative of the primary balloon, the image being prepared from the signals read from the primary measuring means, and the displayed image is observed during dilating of the sphincter.

Preferably, the diameter of the primary balloon at least one transverse cross-section is displayed on the display means.

In another embodiment of the invention a means for stimulating the sphincter to dilate is provided.

Preferably, the means for stimulating the sphincter to dilate comprises a secondary expandable element located on the catheter spaced apart from the primary expandable element, and expandable independently of the primary expandable element.

In another embodiment of the invention the secondary expandable element comprises a secondary inflatable balloon.

Preferably, the secondary expandable balloon defines a hollow interior region with the catheter extending therethrough.

Advantageously, a secondary measuring means is provided for determining the transverse cross-sectional area of the secondary balloon, and for producing a signal indicative of the transverse cross-sectional area of the secondary balloon.

Advantageously, the secondary measuring means is located in the hollow interior region of the secondary balloon.

In another embodiment of the invention the secondary measuring means comprises at least one secondary stimulating electrode on one of the catheter and an inner surface of the secondary balloon and at least one secondary receiving electrode on the one of the catheter and the inner surface of the secondary balloon so that when the secondary balloon is inflated with an electrically conductive medium and one of a stimulating voltage signal and a stimulating current signal is applied to the at least one secondary stimulating electrode, a resulting signal on the at least one secondary receiving electrode is indicative of the transverse cross-sectional area of the secondary balloon adjacent the location of the at least one secondary receiving electrode.

Preferably, the secondary measuring means in the secondary balloon comprises a pair of secondary stimulating electrodes axially spaced apart from each other, and a plurality of axially spaced apart secondary receiving electrodes located between the secondary stimulating electrodes and spaced apart therefrom so that when one of a stimulating voltage signal and a stimulating current signal is applied across the secondary stimulating electrodes when the secondary balloon is inflated with the electrically conductive medium, the resulting signals on the respective secondary receiving electrodes is indicative of the transverse cross-sectional area of the secondary balloon adjacent the respective corresponding secondary receiving electrodes.

Advantageously, the secondary balloon is inflated with an electrically conductive medium, and simultaneously with inflating the secondary balloon the one of the stimulating voltage signal and the stimulating current signal is applied to the at least one secondary stimulating electrode, and the resulting voltage signal is read from the at least one secondary receiving electrode for determining the transverse cross-sectional area of the secondary balloon adjacent the at least one secondary receiving electrodes.

In another embodiment of the invention an image representative of the secondary balloon is prepared from the signals read from the secondary measuring means and the image is observed during inflating of the secondary balloon.

In another embodiment of the invention the diameter of the secondary balloon at least one transverse cross-section is displayed on the display means.

In a further embodiment of the invention the method is adapted for determining the dilating function of a lower oesophageal sphincter, and the method comprises inserting the catheter into the oesophagus with the primary balloon located in the lower oesophageal sphincter and the secondary balloon located in the oesophagus spaced apart from the lower oesophageal sphincter, the primary balloon being inflated to one of a pressure and a volume sufficient to engage the sphincter without dilating the sphincter, and the one of the pressure and the volume is maintained substantially constant so that the primary balloon expands with dilation of the lower oesophageal sphincter, applying the one of the stimulating voltage signal and the stimulating current signal to the at least one primary stimulating electrode, inflating the secondary balloon to simulate a bolus of food in the oesophagus to dilate the sphincter, and reading the resulting signal from the at least one primary receiving electrode as the sphincter dilates for determining the transverse cross-sectional area of the primary balloon adjacent the at least one primary receiving electrode, for in turn determining the transverse cross-sectional area of the lower oesophageal sphincter as it dilates.

Preferably, the one of the stimulating voltage signal and the stimulating current signal is applied to the at least one secondary stimulating electrode while the secondary balloon is being inflated and the resulting signal is read from the at least one secondary receiving electrode for determining the transverse cross-sectional area of the secondary balloon as the secondary balloon is being inflated.

The invention also provides a device for use in a procedure for improving a sealing function of a sphincter, the device comprising a catheter extending between a proximal end and a distal end, a primary expandable element located on the catheter towards the distal end thereof for inserting in the sphincter, and a primary measuring means associated with the primary expandable element for facilitating determining the transverse cross-sectional area of the primary expandable element, the primary expandable element being operable for dilating the sphincter to a desired transverse cross-sectional area, and the primary measuring means being operable for providing an indication of the transverse cross-sectional area of the sphincter while the procedure for improving the sealing function thereof is being carried out.

Further the invention provides a device for testing the dilating function of a sphincter, the device comprising a catheter extending between a proximal end and a distal end, a primary expandable element located on the catheter towards the distal end thereof for inserting in the sphincter, a primary measuring means associated with the primary expandable element for facilitating determining the transverse cross-sectional area of the primary expandable element, and a stimulating means for stimulating the sphincter to dilate, the primary expandable element being operable for progressively expanding with the sphincter as the sphincter is being dilated, and the primary measuring means is operable for providing an indication of the transverse cross-sectional area of the sphincter in response to the stimulation thereof.

Additionally, the invention provides a system for use in a procedure for improving a sealing function of a sphincter, the system comprising a catheter extending between a proximal end and a distal end, a primary expandable element located on the catheter adjacent the distal end thereof for inserting in the sphincter, a primary measuring means associated with the primary expandable element for producing a signal indicative of the transverse cross-sectional area of the primary expandable element, and a control means responsive to signals from the primary measuring means for determining the transverse cross-sectional area of the primary expandable element, the primary expandable element being operable for dilating the sphincter to a desired transverse cross-sectional area, and the control means producing a signal indicative of the transverse cross-sectional area of the sphincter while the procedure for improving the sealing function of the sphincter is being carried out.

The invention also provides a system for testing the dilating function of a sphincter, the system comprising a catheter extending between a proximal end and a distal end, a primary expandable element located on the catheter adjacent the distal end thereof for inserting in the sphincter, a primary measuring means associated with the primary expandable element for producing a signal indicative of the transverse cross-section of the primary expandable element, and a control means responsive to signals from the primary measuring means for determining the transverse cross-sectional area of the primary expandable element, a stimulating means for stimulating the sphincter to dilate, the primary expandable element being operable for progressively expanding with the sphincter as the sphincter is being dilated, and the control means produces a signal indicative of the transverse cross-sectional area of the sphincter as the sphincter is dilating.

The advantages of the invention are many. The system and device according to the invention, as well as the method according to the invention provides a surgeon with a positive and accurate indication of the amount to which the sphincter would be permitted to dilate after carrying out the procedure to improve the sealing function of the sphincter. Where the system, device and method are used in a fundoplication procedure, the surgeon is provided with a positive and accurate indication of the amount to which the lower oesophageal sphincter will dilate after the fundoplication procedure has been carried out. This is due to the fact that when wrapping the fundus of the stomach around the lower portion of the oesophagus adjacent the lower oesophageal sphincter, the amount of restriction which will be caused to the sphincter can be monitored as the fundus is being wrapped around the sphincter, and accordingly, the fundus can be sutured at the appropriate placement which permits dilation of the sphincter to the desired transverse cross-sectional area by merely observing the image of the primary expandable element and the relevant diameter values of the balloon adjacent the centre thereof when the centre of the primary balloon is aligned with the sphincter.

A further and important advantage of the invention is that it permits the dilation response of the sphincter to a simulated bolus of food to be tested both during and after the fundoplication procedure.

A particularly important advantage of the system according to the invention is that it permits a visual representation of the expandable element, which should provide a reasonable representation of the transverse cross-sectional area of the sphincter to be viewed by the surgeon or paramedic during carrying out of the procedure for improving the sealing function of the sphincter or enhancing the biomechanical function thereof, and also during testing of the dilating function of the sphincter. Thus, a surgeon can observe the image during the procedure for improving the sealing function of the sphincter, and where the sphincter is being tightened during the procedure, the surgeon can observe how the tightening of the sphincter affects the transverse cross-sectional area thereof, and can set the tightening of the sphincter when the dilated sphincter is at the desired transverse cross-sectional area. Additionally, the surgeon or paramedic, as the case may be, can readily observe the dilating response of the sphincter by observing the image of the balloon as the sphincter is dilating in response to a stimulus.

Figure 2:
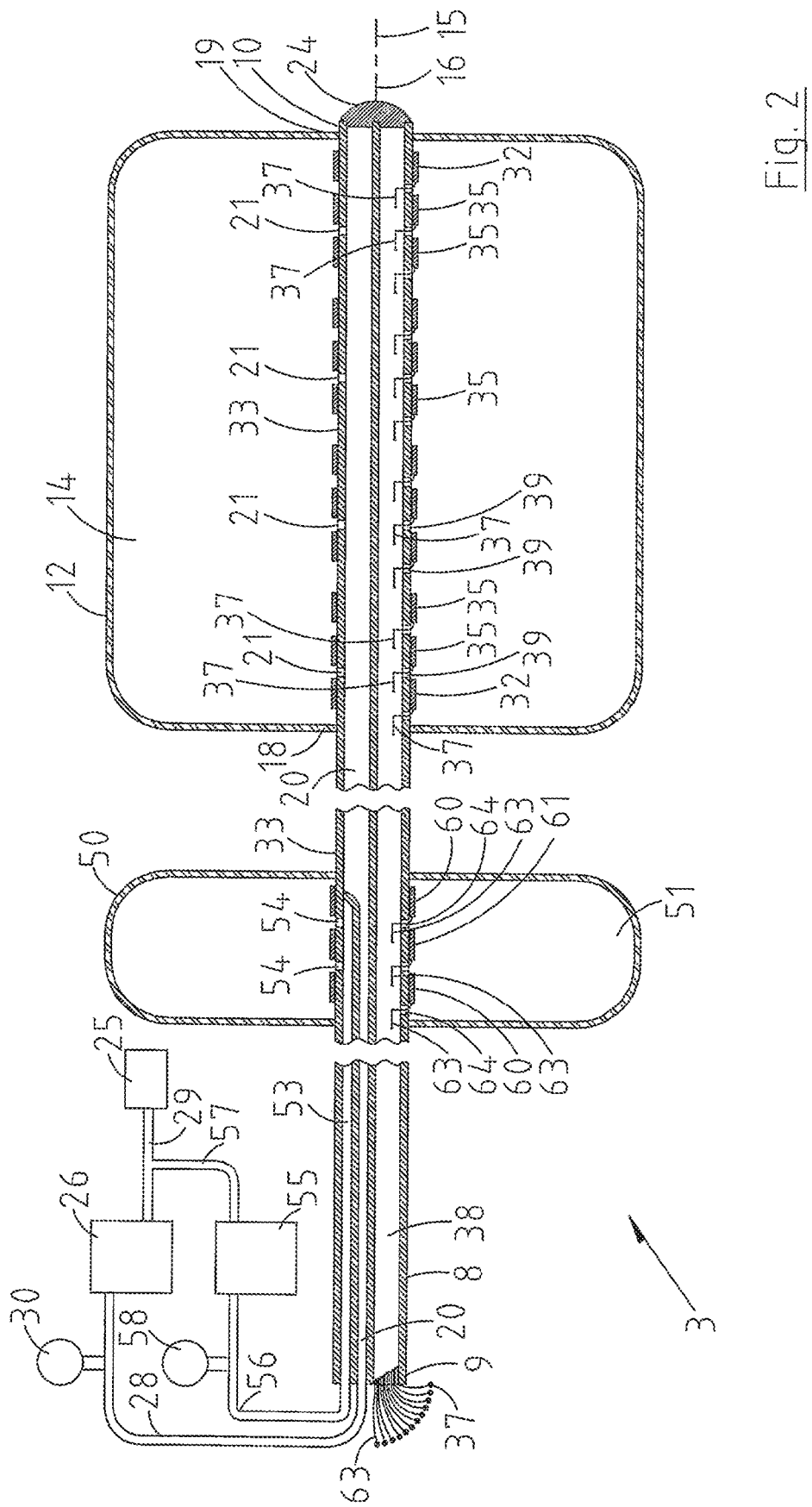
Figure 4:
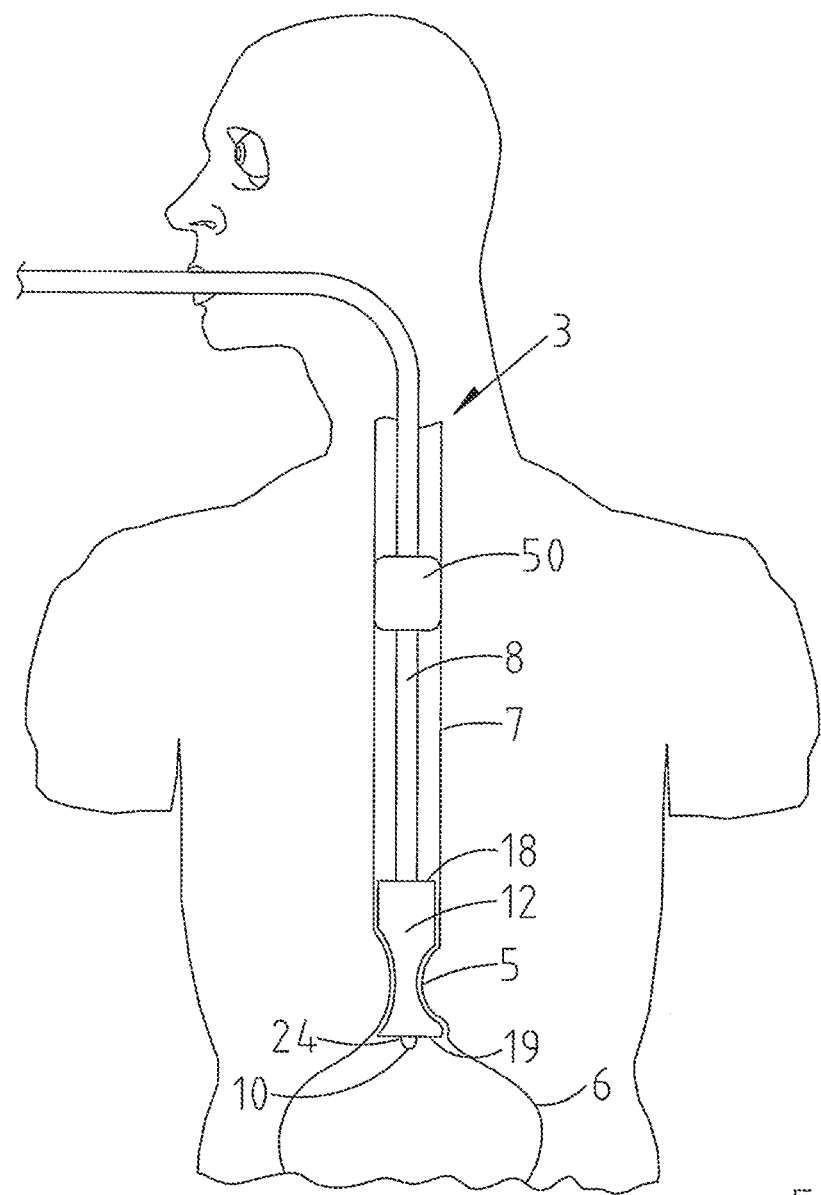
Figure 3:
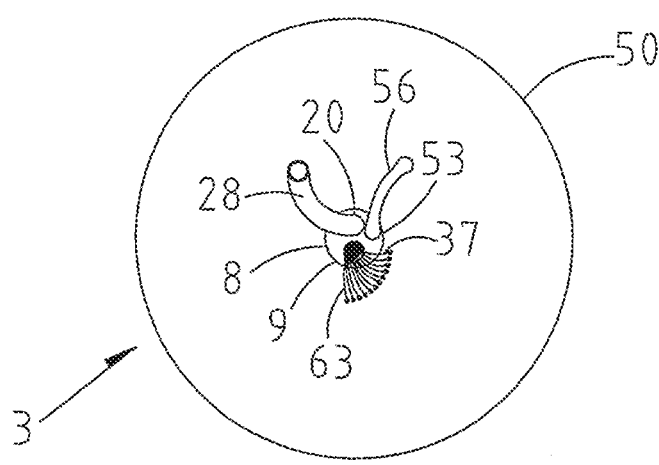

The invention will be more clearly understood from the following description of some preferred embodiments thereof, which are given by way of example only, with reference to the accompanying drawings, in which:

FIG. 1 is a block representational view of a system according to the invention for use in a procedure for improving a sealing function of a sphincter, and which includes a device also according to the invention for use in a procedure for improving the sealing function of a sphincter, FIG. 2 is a transverse cross-sectional elevational view of the device of the system of FIG. 1, FIG. 3 is an end elevational view of the device of FIG. 2, FIG. 4 is a diagrammatic view of the device of FIG. 1 in use, FIG. 5 is a block representation of a system according to another embodiment of the invention for use in a procedure for improving the sealing function of a sphincter, and FIG. 6 is a view similar to FIG. 2 of a device according to another embodiment of the invention for use with the systems of FIGS. 1 and 5 in a procedure for improving the sealing function of a sphincter.

Referring to the drawings and initially to FIGS. 1 to 4 thereof, there is illustrated a system according to the invention, indicated generally by the reference numeral 1, for use in a procedure for improving a sealing function or for enhancing the biomechanical function of a sphincter. The system 1 comprises a device also according to the invention, indicated generally by the reference numeral 3, for use in the procedure. The system 1 and the device 3 in this embodiment of the invention are suitable for use in a fundoplication procedure whereby the sealing function of the lower oesophageal sphincter 5 is corrected. The system 1 also comprises control and analysing apparatus 4, and under the control of the control and analysing apparatus 4 the system 1 and the device 3 are selectively operable in a first mode for dilating the sphincter 5 and in a second mode for testing the dilating response of the sphincter 5 to a simulated bolus of food in the oesophagus 7 as will be described below.

In a fundoplication procedure the fundus, namely, an upper portion of the stomach 6 is wrapped around a lower portion of the oesophagus 7 adjacent the sphincter 5 and sutured in place in order to augment the biomechanical function of the sphincter 5. The device 3 dilates the sphincter 5 to a desired transverse cross-sectional area and displays an image which is representative of the transverse cross-sectional area of the sphincter while the procedure is being carried out, which can be observed by the surgeon carrying out the procedure as the fundus is being tightened around the oesophagus 7 adjacent the sphincter 5, so that the surgeon can observe the effect of tightening of the fundus around the oesophagus on the sphincter, and can suture the fundus when the dilated sphincter 5 is at the desired transverse cross-sectional area. This, thus, avoids over-tightening of the fundus around the sphincter 5. The system 1 and the device 3 are also suitable for testing dilation of the sphincter 5 of the fundoplication procedure as will be described below. Before describing the system 1 in further detail, the device 3 will first be described.

The device 3 comprises an elongated catheter 8 extending from a proximal end 9 to a distal end 10 for inserting into the oesophagus 7 nasally or orally. A primary expandable element, namely, an inflatable primary balloon 12 defining a hollow interior region 14 is located on the catheter 8 adjacent the distal end 10 thereof with the catheter 8 extending through the hollow interior region 14 thereof. In this embodiment of the invention the primary balloon 12 when inflated is of cylindrical configuration and defines a central longitudinally extending balloon axis 15 which coincides with a longitudinally extending central axis 16 of the catheter 8. The primary balloon 12 is sealably secured to the catheter 8 at its respective opposite ends 18 and 19, and is provided thereon for locating within the sphincter 5 for dilating the sphincter 5 to the desired transverse cross-sectional area during the fundoplication procedure. The primary balloon 12 is also operable, as will be described below, when inflated to expand with the sphincter 5 so that the transverse cross-sectional area to which the sphincter 5 dilates when stimulated to dilate can be determined.

A primary inflating medium accommodating means, in this embodiment of the invention an elongated primary axial communicating bore 20 extends longitudinally through the catheter 8 from the proximal end 9 to the distal end 10 thereof for accommodating an inflating medium, which in this case is an electrically conductive medium, and preferably, a saline solution, for inflating the primary balloon 12. A plurality of primary radial communicating bores 21 extend radially through the catheter 8 within the hollow interior region 14 of the primary balloon 12, and communicate with the primary axial communicating bore 20 for accommodating the inflating medium between the primary axial communicating bore 20 and the hollow interior region 14 of the primary balloon 12. The catheter 8 terminates in an epoxy plug 24 which sealably closes the distal end of the primary axial communicating bore 20.

A primary inflating means for inflating the primary balloon 12 with the inflating medium comprises a primary pump 26 located in the control and analysing apparatus 4 which pumps the inflating medium between a reservoir 25 and the primary balloon 12 for inflating and deflating the balloon 12. The primary pump 26 is operated under the control of the control and analysing apparatus 4 as will be described below, and is coupled to the primary axial communicating bore 20 at the proximal end 9 of the catheter 8 by a conduit 28 and to the reservoir 25 by a conduit 29. A primary pressure monitoring means comprising a primary pressure sensor and a primary pressure gauge 30 in the conduit 28 monitors the pressure of the inflating medium in the conduit 28 and in turn in the hollow interior region 14 of the primary balloon 12.

A primary measuring means for determining the transverse cross-sectional area of the primary balloon 12 at axially spaced apart locations along the central axis 15 thereof comprises a pair of axially spaced apart mutually insulated electrically conductive stimulating electrodes 32 located on an outer surface 33 of the catheter 8 for receiving a stimulating voltage signal or a stimulating current signal from the control and analysing apparatus 4 as will be described below. In this case the stimulating signal is a stimulating current signal of constant known current. The stimulating electrodes 32 are located on the catheter 8 in the hollow interior region 14 of the primary balloon 12 adjacent the respective axially opposite ends 18 and 19 of the primary balloon 12.

A plurality of mutually insulated electrically conductive primary receiving electrodes 35 in this case ten primary receiving electrodes 35 are located axially spaced apart on the outer surface 33 of the catheter 8 within the hollow interior region 14 of the primary balloon 12 and between and spaced apart from the primary stimulating electrodes 32. In this embodiment of the invention the primary stimulating electrodes 32 and the primary receiving electrodes 35 are provided by electrically conductive band electrodes which extend circumferentially around and are bonded to the catheter 8. The primary receiving electrodes 35 are equi-spaced apart from each other, and in this case the spacing between the primary stimulating electrodes 32 and the adjacent primary receiving electrodes 35 is similar to the spacing between the primary receiving electrodes 35.

When the primary balloon 12 is inflated with the electrically conductive medium, resulting voltage signals appear on the primary receiving electrodes 35 in response to the stimulating current signal which is applied to the primary stimulating electrodes 32, and the resulting voltage signals appearing on the primary receiving electrodes 35 are indicative of the transverse cross-sectional area of the primary balloon 12 at the respective axially spaced apart locations corresponding to the locations of the respective primary receiving electrodes 35 along the catheter 8.

A primary electrically conductive means for applying the stimulating current signal to the primary stimulating electrodes 32 and for receiving the resulting voltage signals from the primary receiving electrodes 35 when the primary balloon 8 is inflated with the electrically conductive medium comprises a plurality of mutually insulated electrically conductive primary wires 37 which are electrically coupled to the primary stimulating and receiving electrodes 32 and 35. In this embodiment of the invention a separate primary wire 37 is provided to each primary stimulating electrode 32 and to each primary receiving electrode 35. A primary axial wire accommodating bore 38 extending through the catheter 8 from the proximal end 9 and primary radial wire accommodating bores 39 extending from the primary axial wire accommodating bore 38 into the hollow interior region 14 of the balloon 12 accommodate the primary wires 37 from the proximal end 9 of the catheter 8 to the primary stimulating and receiving electrodes 32 and 35.

A constant current signal generator 40 located in the control and analysing apparatus 4 applies the stimulating current signal to the primary stimulating electrodes 32 under the control of a control means, namely, a microprocessor 43. The microprocessor 43 reads the resulting voltage signals from the primary receiving electrodes 35 from which the microprocessor 43 determines the transverse cross-sectional area and in turn approximate values of the diameter of the balloon 12 at the respective axially spaced apart locations corresponding to the respective locations of the primary receiving electrodes 35.

A visual display means, namely, a visual display screen 45 in the control and analysing apparatus 4 under the control of a graphics processor 46 displays an image 47 which is representative of the primary balloon 12. Additionally, under the control of the graphics processor 46 the respective diameters of the primary balloon 12 at the axial spaced apart locations corresponding to the locations of the primary receiving electrodes 35 are displayed in windows 48 on the visual display screen 45 adjacent the corresponding location relative to and adjacent the image 47. The computed values of the diameter of the primary balloon 12 at the locations corresponding to the locations of the primary receiving electrodes 35 which are determined by the microprocessor 43 are applied to the graphics processor 46, which in turn generates the image 47 representative of the primary balloon 12 for display on the visual display screen 45 along with the diameter values in the windows 48.

The signals from the primary receiving electrodes 35 are applied to respective analogue-to-digital converters 49 in the control and analysing apparatus 4, and the digital values of the voltage signals are read from the corresponding analogue-to-digital converters 49 by the microprocessor 43, which in turn determines the respective values of the transverse cross-sectional area of the primary balloon 12 and in turn the corresponding approximate values of the diameter of the primary balloon 12 at the locations corresponding to the locations of the receiving electrodes 35.

The primary pump 26 is also operated under the control of the microprocessor 43 for inflating and deflating the primary balloon 12 and for controlling the volume and pressure to which the primary balloon 12 is inflated in response to signals from the primary pressure sensor and gauge 30, which are read by the microprocessor 43.

A secondary expandable element, namely, a secondary inflatable balloon 50 defining a hollow interior region 51 is located on the catheter 8 spaced apart from the primary balloon 12 intermediate the proximal end 9 of the catheter 8 and the primary balloon 12 with the catheter 8 extending through the hollow interior region 51 of the secondary balloon 50. The secondary balloon 50 when inflated is of cylindrical configuration. In this embodiment of the invention the secondary balloon 50 is located on the catheter 8 at a distance of approximately 200 mm from the primary balloon 12, so that when the primary balloon 12 is axially centrally located in the sphincter 5 the secondary balloon 50 is located in the oesophagus for simulating a bolus of food in the oesophagus 7 upstream of the sphincter 5. The simulation of the bolus of food in the oesophagus by the secondary balloon 50 stimulates the sphincter 5 to dilate, so that with the primary balloon 12 located in the sphincter 5, the amount by which the sphincter 5 dilates in response to the simulated bolus of food can be determined, in order to permit a surgeon to test the tightness to which the fundus has been tightened around the oesophagus 7 adjacent the sphincter 5. This test can be carried out either during or subsequent to the fundoplication procedure. The use of the system 1 and the device 5 for determining the transverse cross-sectional area to which the sphincter 5 dilates in response to a simulated bolus of food is described in more detail below.

A secondary inflating means for inflating the secondary balloon 50 independently of the primary balloon 12 comprises a secondary pump 55 located in the control and analysing apparatus 4, which is operated under the control of the microprocessor 43. A secondary axial communicating bore 53 extending through the catheter 8 from the proximal end 9 thereof and a pair of secondary radial communicating bores 54 which communicate the secondary axial communicating bore 53 with the hollow interior region 51 of the secondary balloon 50. The secondary axial communicating bore 53 is isolated from the primary axial communicating bore 20. The secondary pump 55 delivers the inflating medium between the reservoir 25 and the hollow interior region 55 of the secondary balloon 50 through the axial secondary communicating bore 5 and the radial secondary communicating bores 54 for inflating and deflating the secondary balloon 50. A conduit 56 couples the secondary pump 55 and the secondary axial communicating bore 53 adjacent the proximal end 9 thereof. A conduit 57 couples the reservoir 25 to the secondary pump 55. A secondary pressure monitoring means comprises a secondary pressure sensor and a secondary pressure gauge 58 located on the conduit 56 for displaying the pressure of the inflating medium in the conduit 56, and in turn the pressure of the inflating medium in the secondary balloon 50. The microprocessor 43 reads signals from the secondary pressure sensor and gauge 58 for controlling the pressure to which the secondary balloon 12 is inflated.

In this embodiment of the invention a secondary measuring means provided by a pair of axially spaced apart secondary stimulating electrodes 60 located on the outer surface 33 of the catheter 8 in the hollow interior region 51 of the secondary balloon 50. One secondary receiving electrode 61 is located on the outer surface 33 of the catheter 8 between the secondary stimulating electrodes 60 and equi-spaced apart from the respective secondary electrodes 60. The secondary stimulating electrodes 60 and the secondary receiving electrode 61 are similar to the primary stimulating electrodes 32 and the primary receiving electrodes 35, respectively, and their use in determining the transverse cross-sectional area of the secondary balloon 50 adjacent the secondary receiving electrode 61 is similar to the use of the primary stimulating and receiving electrodes 32 and 35 in determining the transverse cross-sectional area of the primary balloon adjacent the locations of the primary receiving electrodes 35.

A secondary communicating means, namely, mutually insulated secondary electrically conductive wires 63 which are electrically coupled to the secondary stimulating and receiving electrodes 60 and 61 are accommodated through secondary radial wire accommodating bores 64 into the primary axial wire accommodating bore 38 to the proximal end 9 thereof. The secondary wires 63 which are electrically coupled to the secondary stimulating electrodes 60 are coupled to the constant current signal generator 40 for applying a stimulating constant current signal to the secondary stimulating electrodes 60 under the control of the microprocessor 43. The secondary wire 63 which is coupled to the secondary receiving electrode 61 is coupled to an analogue-to-digital converter 65 for converting the resulting voltage signal on the secondary receiving electrode 61 in response to the stimulating current signal applied to the secondary stimulating electrode 60 to a digital value. The microprocessor 43 reads the digital value of the resulting voltage signal from the analogue-to-digital converter 65, and determines the transverse cross-sectional area of the secondary balloon 50 therefrom adjacent the secondary receiving electrode 60, and in turn an approximate value of the diameter of the secondary balloon 50. The microprocessor 43 applies the computed value of the diameter of the secondary balloon 50 to the graphics processor 46, which in turn displays an image 67 which is representative of the secondary balloon 50 on the visual display screen 45 as well as the diameter value thereof in a window 68.

In this embodiment of the invention to ensure that the primary and secondary balloons 12 and 50 are independently inflatable relative to each other, the primary and secondary wires 37 and 63 are sealed in the corresponding primary and secondary radial wire accommodating bores 39 and 64 in order to avoid inflating medium from the hollow interior regions 14 and 51 of the respective primary and secondary balloons 12 and 50 leaking into the primary axial wire accommodating bore 38, and in turn between the respective primary and secondary balloons 12 and 50, respectively.

While in this embodiment of the invention the secondary balloon 50 has been provided with a secondary measuring means in the form of the secondary stimulating and receiving electrodes 60 and 61, in many cases, it will not be necessary to know the diameter to which the secondary balloon 50 is inflated, and in such cases, the secondary measuring means, including the secondary stimulating and receiving electrodes 60 and 61 may be omitted.

In use, with the device 3 coupled to the control and analysing apparatus 4 so that the primary and secondary pumps 26 and 55 are coupled to the primary and secondary axial communicating bores 20 and 53, respectively, and the primary and secondary wires 37 and 63 which are coupled to the primary and secondary stimulating electrodes 32 and 60 coupled to the constant current signal generator 40, and the primary and secondary wires 37 and 63 which are coupled to the primary and secondary receiving electrodes 35 and 61 coupled to the analogue-to-digital converters 49 and 65, respectively, the control and analysing apparatus 4 and the device 3 are ready for use. With the primary and secondary balloons 12 and 50 deflated, the distal end 10 of the catheter 8 of the device 3 is entered into the oesophagus 7 either nasally or orally, and is urged downwardly through the oesophagus 7 until the primary balloon 12 is located in and engaged by the sphincter 5.

When it is desired to maintain the sphincter 5 dilated during a fundoplication procedure, the system 1 and the device 3 are operated in the first mode. The primary pump 26 under the control of the microprocessor 43 is operated to commence inflating the primary balloon 12 with the electrically conductive medium, which in this case is the saline solution from the reservoir 25. Simultaneously the microprocessor 43 activates the constant current signal generator 40 for generating the stimulating current signal which is applied to and maintained on the primary stimulating electrodes 32. The microprocessor 43 reads the digital values of the resulting voltage signals on the primary receiving electrodes 35 from the analogue-to-digital converters 49, and determines both the transverse cross-sectional area of the primary balloon 12 and the approximate values of the diameter of the primary balloon 12 at the axially spaced apart locations corresponding to the locations of the receiving electrodes 35. The values of the transverse cross-sectional area and the values of the diameter of the primary balloon 12 at the respective axially spaced apart locations are applied to the graphics processor 46, which generates the image 47 which is representative of the primary balloon 12, and which is displayed on the visual display screen 45 along with the corresponding diameter values in the windows 48.

As the primary balloon 12 is being inflated, the image 47 and the diameter values in the windows 48 are continuously updated. During initial inflation of the primary balloon 12, the catheter 8 is maneuvered so that the primary balloon 12 is centred axially within the sphincter 5, in other words, so that the sphincter 5 engages the outer surface of the primary balloon 12 centrally equi-spaced from the axial opposite ends 18 and 19 of the primary balloon 12. A surgeon carrying out the fundoplication procedure observes the visual display screen 45 and when the transverse cross-sectional area of the primary balloon 12 at the location of the sphincter corresponds to the desired diameter to which the sphincter is to be dilated, the primary pump 26 is operated for maintaining the volume of the primary balloon 12 substantially constant, and in turn the transverse cross-sectional area of the primary balloon 12 substantially constant for in turn maintaining the sphincter dilated to the desired diameter. The desired diameter to which the sphincter is to be dilated is typically 10 mm to 20 mm.

Once the diameter of the sphincter 5 is being maintained constant by the primary balloon 12, the surgeon wraps the fundus of the stomach around the lower portion of the oesophagus 7 adjacent the sphincter 5. As the fundus is being manipulated around the oesophagus, the diameter of the primary balloon 12 adjacent the location of the sphincter 5 is observed on the visual display screen 45. During this part of the procedure as the fundus is being tightened around the oesophagus, the diameter of the primary balloon 12 varies as the fundus is tightened or loosened. Tightening or loosening of the fundus continues until the diameter of the primary balloon 12 adjacent the sphincter 5 is at the diameter value at which the fundus is to be sutured, and the fundus is then sutured. Since the primary balloon 12 is inflated and is located in the sphincter 5, the diameter of the balloon 12 adjacent the sphincter 5 is similar to the diameter of the sphincter 5.

When the fundoplication procedure has been completed, the primary balloon 12 is deflated, and if desired, at that stage the catheter 8 is removed from the subject with the primary and secondary balloons 12 and 50 deflated.

However, if it is desired to test the dilation response of the sphincter 5 to a simulated bolus of food, the system 1 and the device 3 are operated in the second mode. The primary balloon 12 is again inflated with the saline solution by the primary pump 26 to a pressure or volume sufficient to engage the sphincter without dilating the sphincter 5, but sufficient such that as the sphincter 5 dilates, the portion of the primary balloon 12 adjacent the sphincter 5 expands with the sphincter 5, so that the transverse cross-sectional area of the sphincter 5 can be determined from the transverse cross-sectional area of the balloon 12 adjacent the sphincter 5. During this inflation of the primary balloon 12 the pressure of the saline solution in the primary balloon 12 is monitored on the primary pressure sensor and gauge 30 by the microprocessor 43, which appropriately operates the primary pump 26 in response to the monitored pressure. Once inflating of the primary balloon 12 commences, the signal generator 40 is operated to apply and maintain the stimulating current signal on the primary stimulating electrodes 32 so that the diameter of the primary balloon can be determined at the axially spaced apart locations corresponding to the primary receiving electrodes 35. The image 47 of the primary balloon 12 and the respective diameter values thereof are displayed and continuously updated on the visual display screen 45. The secondary balloon 50 is then inflated with the saline solution by the secondary pump 55 to simulate a bolus of food in the oesophagus. During inflating of the secondary balloon 50, the stimulating current signal is applied to the secondary stimulating electrodes 60 and the resulting voltage signal on the secondary receiving electrode 61 is read from the analogue-to-digital converter 65 by the microprocessor 43. The image 67 of the inflating secondary balloon 50 is displayed and continuously updated on the visual display screen 45 along with the diameter thereof, which is displayed in the window 68. When the secondary balloon 50 has been inflated sufficiently to simulate a bolus of food, the dilating response of the sphincter 5 to the simulated bolus of food is observed on the visual display screen 45. If the sphincter 5 dilates to the desired diameter, the fundus is deemed not to have been over-tightened around the sphincter 5, thus allowing a bolus of food to pass through the sphincter 5 into the stomach.

When testing of the dilating response of the sphincter to the bolus of food has been completed, the primary and secondary balloons 12 and 50 are deflated and the catheter 8 is removed from the oesophagus.

During inflating of the secondary balloon 50, the pressure of the saline solution therein is monitored on the secondary pressure sensor and gauge 58 in order to ensure against excessive pressure on the wall of the oesophagus.

It will be appreciated that the system 1 and the device 3 may be used at any time for testing the dilating response of a lower oesophageal sphincter to a simulated bolus of food, irrespective of whether a fundoplication procedure has been carried out.

In this embodiment of the invention the microprocessor 43 is programmed to determine the values of the transverse cross-sectional area and the values of the diameter of the primary balloon 12 at the locations corresponding to the locations of the primary receiving electrodes 35 by determining the voltage drop between adjacent ones of the primary receiving electrodes 35 and the voltage drop between the primary stimulating electrodes 32 and the adjacent primary receiving electrodes 35. Due to the fact that the voltage drops between the adjacent primary receiving electrodes 35 and between the primary stimulating and receiving electrodes 32 and 35 is a function of the impedance of the saline solution between the respective primary stimulating and receiving electrodes 32 and 35, the values of the transverse cross-sectional area and the diameter of the primary balloon 12 adjacent the corresponding primary receiving electrodes 35 is a function of the voltage values thereon. The value of the transverse cross-sectional area of the secondary balloon 50 adjacent the secondary receiving electrode 61 is similarly determined by the microprocessor 43 as a function of the corresponding voltage drop between the secondary stimulating and receiving electrodes 60 and 61.

Referring now to FIG. 5, there is illustrated a system also according to the invention, indicated generally by the reference numeral 70, also for use in carrying out a fundoplication procedure. The system 70 is substantially similar to the system 1 and similar components are identified by the same reference numerals. The system 70 comprises a device also for use in the fundoplication procedure which is identical to the device 3 described with reference to FIGS. 1 to 4. The only difference between the system 70 and the system 1 is in the application of the voltage signals from the primary receiving electrodes 35 to the microprocessor 43. In this embodiment of the invention the voltage signals from the primary receiving electrodes 35 are differentially applied to the analogue-to-digital converters 49 through differential op-amps 71. The inverting and non-inverting inputs of the op-amps 71 are coupled to adjacent ones of the primary receiving electrodes 35, and the outputs of the differential op-amps 71 are applied to the corresponding analogue-to-digital converters 49, from which the digital values of the differential voltages are read by the microprocessor 43. Otherwise, the system 70 and its use is similar to the system 1 and the device 3.

Referring now to FIG. 6, there is illustrated a device according to another embodiment of the invention, indicated generally by the reference numeral 80, also for use in a fundoplication procedure and for use in conjunction with either the system 1 or the system 70 described with reference to FIGS. 1 to 4, and FIG. 5, respectively. The device 80 is substantially similar to the device 3 described with reference to FIGS. 1 to 4 and similar components are identified by the same reference numerals. The main difference between the device 80 and the device 1 is that in this embodiment of the invention the primary expandable element is provided in the form of three primary balloons 12a, 12b and 12c. The primary balloons 12a, 12b and 12c are inflatable independently of each other by three primary pumps (not shown) which are provided in the control and analysing apparatus 4. Three mutually isolated primary axial communicating bores and primary radial communicating bores are provided in the catheter 8 for communicating the respective primary balloons 12 with the corresponding primary pumps 26. Each primary balloon 12 is provided with a primary measuring means which includes a pair of primary stimulating electrodes 32 and a plurality of primary receiving electrodes 35 similar to and similarly spaced as the primary stimulating electrodes 32 and receiving electrodes 35 of the device 3 for facilitating a determination of the respective transverse cross-sectional areas and diameters of the respective balloons 12 at locations corresponding to the respective primary receiving electrodes 35.

The use of the device 80 is substantially similar to that of the device 3. However, the advantage of providing the expandable element in the form of three primary balloons 12 facilitates a more accurate placement of the device 80 in the sphincter 5, so that the central primary balloon 12b is axially aligned with the sphincter 5, and furthermore, the provision of the three primary balloons 12 also facilitates a more accurate determination of the dilated diameter of the sphincter 5, as well as more accurate dilating of the sphincter 5.

Otherwise, use of the device 80 is similar to that of the device 3.

While the systems and devices have been described for use for dilating the lower oesophageal sphincter at a desired transverse cross-sectional area during a fundoplication procedure, it will be readily apparent to those skilled in the art that the device may be used for dilating any sphincter during the carrying out of any procedure on the sphincter. It will also be readily apparent to those skilled in the art that the systems and devices may also be used for testing the dilating response of any other sphincter in response to stimulation. Indeed, it will be readily apparent to those skilled in the art that the system and device, and the method according to the invention may be used for dilating the lower oesophageal sphincter to a desired transverse cross-sectional area during any other type of procedure for improving the sealing function of the lower oesophageal sphincter or for enhancing the biomechanical function of the lower oesophageal sphincter.

While the device 3 has been described as being provided with ten primary receiving electrodes, any number of primary receiving electrodes may be provided, and the number of primary receiving electrodes will largely depend on the length of the primary balloon, and the resolution required. Additionally, while two primary stimulating electrodes have been provided in the device 3 and 80, in certain cases, a single primary stimulating electrode may be sufficient.

While the secondary balloons have been described as comprising secondary stimulating and receiving electrodes for facilitating a determination of the diameter of the secondary balloon, in certain cases, it is envisaged that the secondary stimulating and receiving electrodes may be omitted, and if it were desired to determine the diameter to which the secondary balloons are inflated, the diameter could be determined by monitoring the pressure to which the secondary balloon is inflated on the second pressure sensor and gauge. In cases where secondary stimulating and receiving electrodes are omitted from the secondary balloon, the inflating medium may be a non-electrically conductive medium.

It will also be appreciated in certain embodiments of the invention the secondary balloon may be omitted, where the systems and devices are solely provided for the purpose of dilating the sphincter to a desired transverse cross-sectional area prior to and during a fundoplication procedure.

It will of course be appreciated that any suitable electrically conductive inflating media besides a saline solution may be used for inflating both the primary balloon and the secondary balloon, and as discussed above, in certain cases, the inflating medium for inflating the secondary balloon may be a non-electrically conductive inflating medium.

While a primary and secondary inflating means have been described as being provided by separate pumps, it is envisaged in certain cases, that a single pump may be provided for inflating the respective primary and secondary balloons with the inflating medium, and in which case, a suitable valving system would be provided for facilitating independent inflating of the primary and secondary balloons by the single pump.

While the images representative of the primary and secondary balloons displayed on the visual display screen has been described as being a three-dimensional image, it will readily be apparent to those skilled in the art that any suitable image representative of the balloons may be provided, for example, a longitudinal cross-sectional profile, or any other suitable image. However, it will be appreciated that the images, while they will be representative of the balloons, and may be representative of a three-dimensional images of the respective balloons or longitudinal external profiles of the respective balloons, the images may not be exact images, since while the balloons when inflated in free air will inflate to a cylindrical configuration, nonetheless, the balloons are of a deformable material, and thus, will adopt the shape of the sphincter or oesophagus within which they are located, which may not be entirely of circular cross-section, and thus, the images produced on the display screen, while they will be a reasonable representation of the balloons, will not be an exact representation of the balloons.

While the balloons have been described as being of cylindrical configuration when inflated, the balloons may be of any other shape, and may be of any other transverse cross-section besides circular. For example, the balloons when inflated may be of square, rectangular, triangular, hexagonal, polygonal or any other desired transverse cross-section, and in certain cases, it is envisaged that the transverse cross-section of the balloons may be matched to the cross-section of the lumen or cavity into which they are to be inserted.

While respective wires from the primary receiving electrodes have been described as extending through the catheter for coupling the primary receiving electrodes to the corresponding analogue-to-digital converters in the control and analysing apparatus, it is envisaged in certain cases that the number of primary wires may be reduced, and in certain cases, may be reduced to one primary wire. In which case, the signals on the primary receiving electrodes would be multiplexed along the single wire, or the few wires to the corresponding analogue-to-digital converter. Similarly, a single wire may be provided for coupling the secondary receiving electrodes in the secondary balloon to the corresponding analogue-to-digital converter or converters, and multiplexing, likewise, would be carried out. In such cases, it is envisaged that the multiplexer would be provided in the balloon or balloons, as the case may be, or in the catheter adjacent the balloon or balloons, as the case may be.

The invention claimed is:

1. A method for improving the sealing function of the lower oesophageal sphincter in a fundoplication procedure, the method comprising:
    providing a dilation response testing device comprising an elongated catheter extending between a proximal end and a distal end, a primary inflatable balloon defining a hollow interior region located on the catheter towards the distal end thereof, a primary measuring device located in the hollow interior region of the balloon to produce signals indicative of the transverse cross-sectional area of the balloon, and a secondary inflatable balloon defining a hollow interior region located on the catheter intermediate the primary balloon and the proximal end of the catheter and axially spaced apart from the primary balloon,
the method further comprising:
locating the dilation response testing device in the oesophagus with the primary balloon located in the lower oesophageal sphincter and the secondary balloon located in the oesophagus spaced apart from the lower oesophageal sphincter,
selectively operating the dilation response testing device in one of
a first mode during the fundoplication procedure by inflating the primary balloon to dilate the lower oesophageal sphincter to a desired transverse cross-section, and maintaining the primary balloon inflated to maintain the lower oesophageal sphincter dilated to the desired transverse cross-section while the fundoplication procedure is being carried out, and
a second mode on completion of the fundoplication procedure to determine the dilation response of the lower oesophageal sphincter, by inflating the primary balloon to engage the lower oesophageal sphincter without dilating the sphincter, maintaining the primary balloon inflated so that the primary balloon expands with the lower oesophageal sphincter as the lower oesophageal sphincter dilates,
inflating the secondary balloon to simulate a bolus of food in the oesophagus, and
monitoring the dilation response of the sphincter to the simulated bolus of food by reading signals from the primary measuring device to determine the transverse cross-sectional area of the sphincter.

2. A method as claimed in claim 1 in which the diameter of the primary balloon at at least one transverse cross-section is displayed on a visual display screen while the device is being operated in the first and second modes in response to the signals produced by the primary measuring device.

3. A method as claimed in claim 2 in which an image representative of the primary balloon prepared from the signals produced by the primary measuring device is displayed on the visual display screen while the device is being operated in the first and second modes.

* * * * *